US008043376B2

(12) United States Patent
Falahee

(10) Patent No.: US 8,043,376 B2
(45) Date of Patent: Oct. 25, 2011

(54) PERCUTANEOUS POSTERIOR LATERAL IN-SITU CAGE

(75) Inventor: Mark H. Falahee, Ann Arbor, MI (US)

(73) Assignee: US Spine, Inc., Salt Lake City, UT (US)

( * ) Notice: Subject to any disclaimer, the term of this patent is extended or adjusted under 35 U.S.C. 154(b) by 1962 days.

(21) Appl. No.: 10/979,021

(22) Filed: Nov. 1, 2004

(65) Prior Publication Data

US 2005/0143819 A1 Jun. 30, 2005

Related U.S. Application Data

(63) Continuation-in-part of application No. 10/462,498, filed on Jun. 16, 2003, now Pat. No. 7,674,297.

(60) Provisional application No. 60/516,209, filed on Oct. 31, 2003, provisional application No. 60/388,974, filed on Jun. 14, 2002.

(51) Int. Cl.
*A61F 2/44* (2006.01)
(52) U.S. Cl. ..................... 623/17.11; 606/99
(58) Field of Classification Search .... 623/17.11–17.16; 606/61, 99
See application file for complete search history.

(56) References Cited

U.S. PATENT DOCUMENTS

| | | | |
|---|---|---|---|
| 5,514,180 A | 5/1996 | Heggeness et al. ............... 623/17 |
| 5,665,122 A | 9/1997 | Kambin ............................ 623/17 |
| 5,980,522 A * | 11/1999 | Koros et al. ..................... 606/61 |
| 6,039,761 A * | 3/2000 | Li et al. ........................ 623/17.16 |
| 6,086,613 A * | 7/2000 | Camino et al. ............. 623/17.16 |
| 6,159,244 A * | 12/2000 | Suddaby .................... 623/17.11 |
| 6,174,334 B1 * | 1/2001 | Suddaby .................... 623/17.11 |
| 6,193,757 B1 * | 2/2001 | Foley et al. ................ 623/17.16 |
| 6,478,823 B1 * | 11/2002 | Michelson ................ 623/17.16 |
| 6,613,089 B1 | 9/2003 | Estes et al. ...................... 623/17 |
| 6,648,917 B2 * | 11/2003 | Gerbec et al. ............. 623/17.11 |
| 6,723,126 B1 | 4/2004 | Berry ............................... 623/17 |
| 6,852,129 B2 * | 2/2005 | Gerbec et al. ............. 623/17.15 |
| 6,863,673 B2 * | 3/2005 | Gerbec et al. .................... 606/99 |
| 6,953,477 B2 * | 10/2005 | Berry .......................... 623/17.11 |
| 7,008,453 B1 * | 3/2006 | Michelson ................ 623/17.16 |
| 2002/0068977 A1 * | 6/2002 | Jackson ..................... 623/17.15 |
| 2002/0143401 A1 * | 10/2002 | Michelson ................ 623/17.16 |
| 2003/0069586 A1 * | 4/2003 | Errico et al. ..................... 606/99 |
| 2004/0167625 A1 * | 8/2004 | Beyar et al. ................ 623/11.11 |

* cited by examiner

*Primary Examiner* — Paul Prebilic
(74) *Attorney, Agent, or Firm* — Matthew D. Thayne; Stoel Rives LLP

(57) ABSTRACT

Implants, tools and techniques facilitate a percutaneous posterior lateral approach to the placement of an in-situ cage, and an inventive cage design to meet this objective. In terms of apparatus, the invention includes a laterally expandable cage, including a locking gate, enabling the system to be introduced into an intradiscal space through a minimally invasive percutaneous posteo-lateral approach. In addition to the cage designs, adapted to hold bone graft and/or other biologic materials, the invention includes other novel instruments, including an introducer associated with cage placement, deployment and closure.

9 Claims, 4 Drawing Sheets

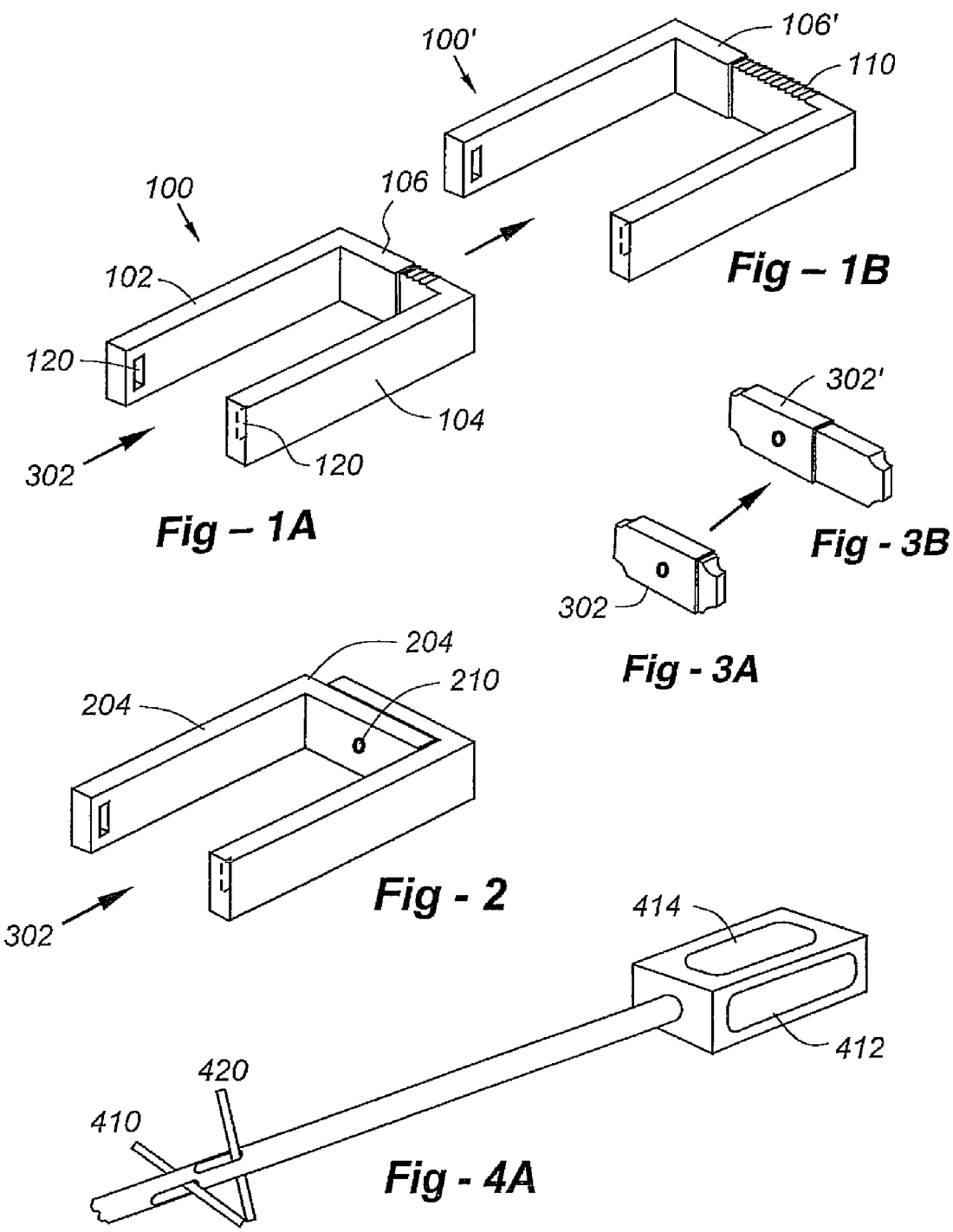

PERCUTANEOUS POSTERIOR LATERAL IN-SITU CAGE

REFERENCE TO RELATED APPLICATION

This application claims priority from U.S. Provisional Patent Application Ser. No. 60/516,209, filed Oct. 31, 2003. This application is also a continuation-in-part of U.S. patent application Ser. No. 10/462,498, filed Jun. 16, 2003 now U.S. Pat. No. 7,674,297, which claims priority from U.S. Provisional Patent Application Ser. No. 60/388,974, filed Jun. 14, 2002. The entire content of each application is incorporated herein by reference.

FIELD OF THE INVENTION

This invention relates generally to development of tools and techniques for percutaneous posterior lateral approach to place a modified in-situ cage.

BACKGROUND OF THE INVENTION

One of the most common causes of chronic back pain is degenerative disc disease. The degeneration may start after a particular injury, or many occur due to multiple injuries over time. Degeneration usually takes several years. As the vertebrae grow closer, the openings in the back of the spine where the nerve roots leave the spinal canal become narrower. This can lead to pinching and irritation on the nerves, causing pain.

There are many surgical approaches and methods used to fuse the spine. Most involve the placement of a bone graft between the vertebrae. Supplemental hardware, such as plates, screws and cages may or may not be used, depending upon the indication.

An early cage design is described in U.S. Pat. No. 4,501,269 to Bagby, entitled "PROCESS FOR FUSING BONE JOINTS." According to the method, a hole is bored transversely across the joint and a slightly larger cylindrical basket is driven into the hole, thereby spreading the bones in resistance to the tensile forces of the surrounding tissue. Immediate stabilization of the joint is achieved by the implantation of the rigid cylindrical basket. Subsequent bone-to-bone fusion is achieved, both through and about the basket, which is filled with bone fragments produced during the boring step.

The Bagby patent states that the process is applicable to any human or animal joint formed by opposed contiguous bony surfaces which are covered and separated by intervening cartilage and are surrounded by ligaments which resist expansion of the joint. Specific examples of such joints are a spinal joint between adjacent vertebrae or the ankle joint.

This stand-alone interbody fusion technique continued to evolve with material changes and the design of threaded cages to increase stability and decrease displacement rates. Bilateral, parallel implants were designed for use in the lumbar spine, with the first human implantation occurring in the early 1009s. The cylindrical titanium cages were threaded to screw into the endplates, thereby stabilizing the device and allowing for increased fusion rate with a stand-alone anterior device.

Ray and colleagues developed a similar titanium interbody fusion device which was initially used in posterior lumbar interbody fusions (PLIF), but expanded to include ALIF procedures (anterior lumbar interbody fusions). In 1985, Otero-Vich reported using threaded bone dowels for anterior cervical arthrodesis, and femoral ring allograft bone has subsequently been fashioned into cylindrical threaded dowels for lumbar application.

Currently, there are a wide number of available interbody fusion devices of varying design and material, including:

1) Cylindrical threaded titanium interbody cages;
2) Cylindrical threaded cortical bone dowels; and
3) Vertical interbody rings, boxes and wedges.

A typical intervertebral fusion cage is a large, hollow cylinder made of some type of metal, usually titanium. It is designed as a "cage" so that bone graft can be placed inside the hollow cylinder. Holes throughout the cage allow bone to form around and through the cage to allow a spinal fusion to occur between two vertebrae. Many of the newer types of intervertebral fusion cages are also designed to facilitate an open incision or a laproscopic procedure.

An intervertebral fusion cage serves a couple important purposes. First, it distracts the vertebrae, making more room for the nerves, thereby decreasing pinching and irritation. The strong ligaments that surround the disc are also tightened, which decreases the segmental instability between the two vertebrae and decreases the mechanical pain in the spine. The cage also hold the two vertebrae in the correct position until a fusion occurs.

There are several drawbacks with existing approaches and techniques, such that further research and improved designs are desirable. Increased morbidity of anterior in-situ cage placement is not justified when less anatomic correction of the disc space is possible. Additionally, current PLIF and transverse lumbar interbody fusions (TLIF) cage and allograft placements require large dissections for exposure. PLIF and TLIF approaches also weaken existing posterior elements via bony destruction resulting from the operative procedure used to access the disc space.

My co-pending U.S. patent application Ser. No. 10/462, 498, incorporated herein by reference, improves upon existing solutions by providing a spinal fusion system including a cage with a fillable volume and removable locking gate. This enables the fillable volume to be packed with graft, biologic or other materials prior to the gate being closed and locked. In the preferred embodiment, the locking gate is positioned anteriorally, though lateral, posterior, and combinations thereof are also possible.

SUMMARY OF THE INVENTION

This invention broadly resides in implants, tools and techniques facilitating a percutaneous posterior lateral approach to the placement of an in-situ cage, and an inventive cage design to meet this objective.

In terms of apparatus, the invention includes a laterally expandable cage, including a locking gate, enabling the system to be introduced into an intradiscal space through a minimally invasive percutaneous posteo-lateral approach.

In addition to the cage designs, adapted to hold bone graft and/or other biologic materials, the invention includes other novel instruments, including an introducer associated with cage placement, deployment and closure.

BRIEF DESCRIPTION OF THE DRAWINGS

FIG. 1A is a perspective view of a preferred laterally expandable cage according to the invention in a collapsed state;

FIG. 1B is a perspective view of a preferred laterally expandale cage according to the invention in an expanded state;

FIG. 2 is a perspective view of an alternate laterally expandable cage;

FIG. 3A is a perspective view of a variable-length locking gate in a collapsed state;

FIG. 3B is a perspective view of a variable-length locking gate in an expanded state;

FIG. 4A is a drawing of an instrument according to the invention that may be used both to overdistract a disc space and expand a novel cage according to the invention

DETAILED DESCRIPTION OF THE INVENTION

Figure 9:
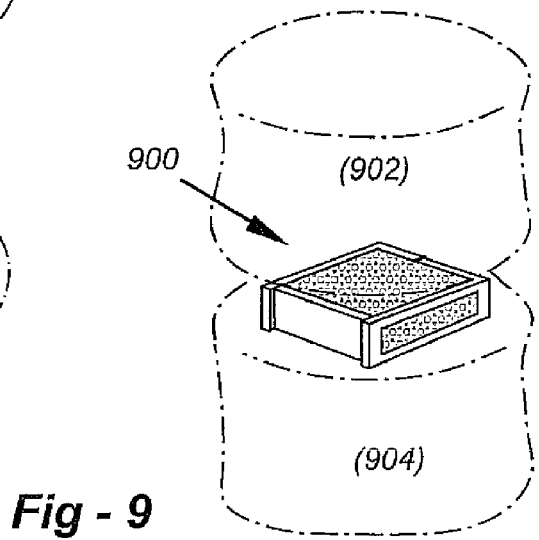
FIG. 9 is a perspective view drawing showing the expanded, filled cage in position between upper and lower vertebral bodies.

This invention resides in an expandable, locking intervertebral cage facilitating a minimally invasive percutaneous posteo-lateral approach. FIG. 9 is a perspective view drawing showing the expanded, filled cage in position between upper and lower vertebral bodies. In this description, the cage designs and novel instruments will first be introduced, followed by a detailed description of the preferred surgical procedure.

The cage is preferably radiolucent, being composed of a carbon fiber, but with one or more radiopaque markers to provide a certain degree of visualization. Full or partial metal or ceramic construction may also be used. Some or all of the walls of the cage may include superior and/or inferior surface features to enhance positioning and/or minimize back-out, and the posterior wall may be indented to prevent neurocompression. The sidewalls of the cage may further include a recessed face with nipple indents and locking fasteners. Multiple cages may provided, each being shaped differently for use at different spinal levels. For example, the cage may be larger and more trapezoidally-pronounced for the L5-S1 levels, or smaller and less trapezoidally pronounced for the T and L2 levels.

FIG. 1A is a perspective view of a preferred laterally expandable cage according to the invention. The cage, depicted generally at 100, includes side arms 102, 104, connected through a back wall 106 which is laterally expandable, creating an adjustable C-shaped implant, As shown in FIG. 1B in the preferred embodiment, the back wall includes ratchets 110 which allow the cage to be expanded but not contracted once in position, leading to an expanded wall 106' associated with the expanded cage 100'.

Note that the forward portions of the arms 102, 104 include indents 120. The purpose of these indents is to receive the ends of an expandable gate described with reference to FIGS. 3A and 3B. FIG. 2 is a drawing which shows an alternate embodiment of a gate according to the invention, wherein arms 204, 206 overlap with one another at the back wall, and one or both includes multiple screw holes such as 210, enabling a fastener to be used to lock the arms into a desired width through the use of an appropriate fastener. Again, the area shown in 302 would be closed with the gate of the type depicted in FIG. 3A, which shows an expandable gate according to the invention, and a collapsed state at 302, and an expanded state at 302', as shown in FIG. 3B. In the preferred embodiment, the gate is spring-loaded to expand into position, facilitating introduction in the collapsed state 302.

Figure 4B:
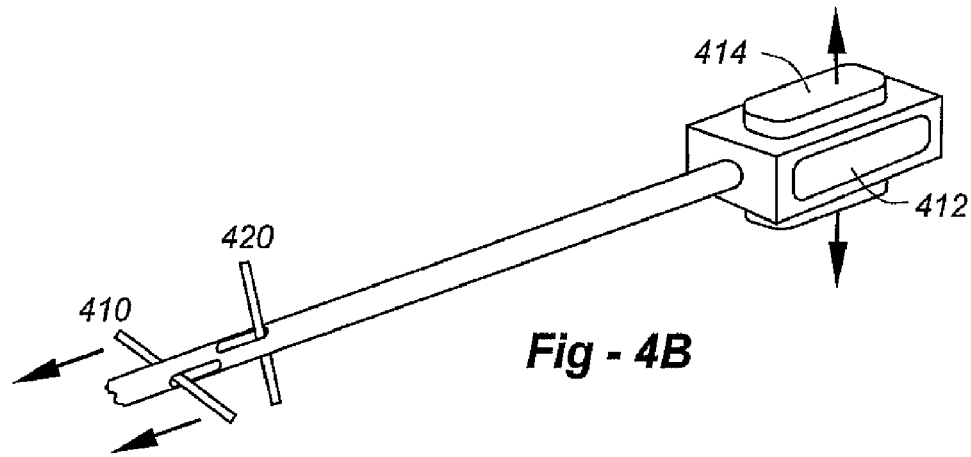
FIG. 4B is a drawing of the expander portion of the device of FIG. 4A, with three millimeters of expansion in both superior and inferior directions.

FIG. 4A is a drawing which shows a multi-purpose distracter/introducer according to the invention. Generally speaking, the tool includes upper and lower expansion portions 402, 404 used to "overdistract" a disc space for tool removal and cage placement, the advancement of these sections being controlled by a manually operated feature 410 which, when pulled toward the user, causes the plates 402, 404 to expand on the order of one to three millimeters or more. The tool further includes side expanders 412, 414 which expand under control of a different manually operated feature 420. FIG. 4B shows the control 410 being pulled, causing the plates 402, 404 to expand outwardly. The tool would be providing in different sizes, with, for example, a height on the eight millimeters for a 10 millimeter cage, 10 millimeters for a 12 millimeter cage, 12 millimeters for a 14 millimeter cage, and so forth, such that through overdistraction on the order of three millimeters in each case, the tool may be removed, leaving the cage in position.

Figure 5A:
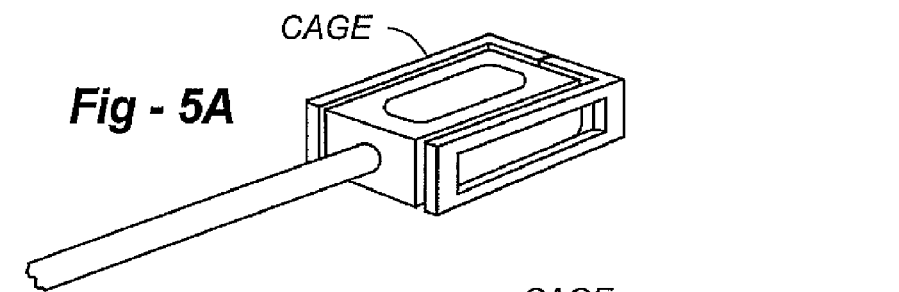
FIG. 5A is a drawing of the device of FIG. 4 with a cage coupled thereto prior to expansion.
Figure 5B:
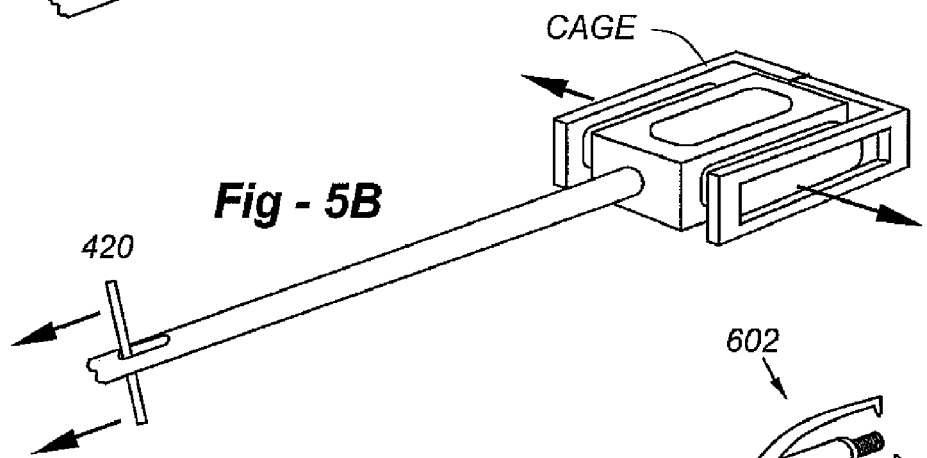
FIG. 5B is a drawing of the device of FIG. 5A, having expanded a cage in position.
Figure 6A:
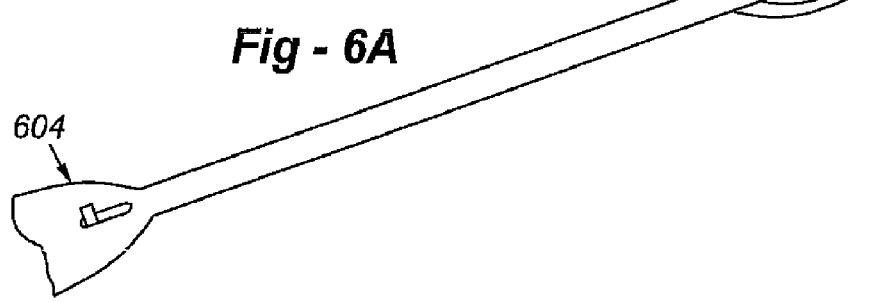
FIG. 6A is a drawing of a gate introducer according to the invention is a predeployed state.
Figure 6B:
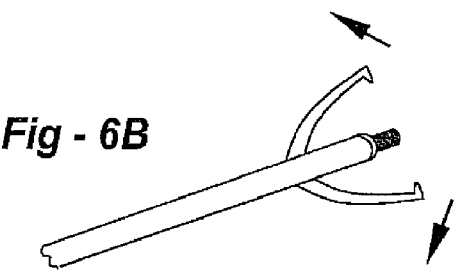
FIG. 6B is a drawing of the introducer of FIG. 6A in an opened state.

FIG. 5A shows a cage of the type in FIGS. 1A, 1B or 2, without the gate of FIGS. 3A and 3B, being loaded onto the tip of the tool, and FIG. 5B shows the cage being expanded through operation of control 20, as described with reference to FIG. 4A. FIG. 6A is a drawing which shows the gate introducer, according to the invention, including a set of claws 602 which are expanded through a control 604, as shown in FIG. 6B. Thus, utilizing the spring-loaded gate of FIGS. 3A and 3B, it may be introduced in a collapsed position, then expanded using the control 604 to leave it in place as discussed in further detail below.

In terms of operative procedure, the patient is under general anesthetic, in a prone position on a C-arm capable table. A surface grid of the type described in my co-pending patent application Ser. No. 10/689,123, or other localizing device, is used to assist with finding anatomic entry point outside pedicle, below the traverse process, and into disc space using a posterior lateral approach (known to those of skill as an IDET approach).

A guide wire is inserted into the disc space using a handheld instrument or assisted using the navigable radiolucent forceps of the type described in my co-pending patent application Ser. No. 10/268,373. A 2-plane check is then carried out using the C-arm to ensure that the tip of the guide wire is in anterior opposite quadrant, with the guide wire parallel to endplates.

A penetrating guide sleeve is placed over the guide wire and advanced to center of disc. The puncture incision is enlarged and a series of soft tissue dilators are inserted to desired mm height (i.e., up to 12 mm for a 12 mm cannula).

A specific sized cannula (ex. 12 mm) is inserted over the dilator and docked onto disc space. The dilator is held against the disc space, and an endoscope is optionally inserted to check anatomic position.

The guide wire and dilator are removed, keeping the cannula against disc space. A sharp coring biopsy tool is then used to create an opening into disc space. Ronguers and/or rasps are inserted, and serrated scrappers are used to remove disc material.

A series of disc space dilators are next inserted up to desired cage height (i.e., 10, 12, 14 mm, color coded). The last dilator is removed and replaced with cage/overdistractor tool of specific cage, loaded with correct, color-coded cage. The cage is oriented with the cage sides facing endplates. This and any of the following steps may be checked with the C-arm, as appropriate. The tool and (attached cage) are rotated 90 degrees, to deploy the side walls and "overdistract" by 1-4 mm over the actual height of cage.

Figure 7D:
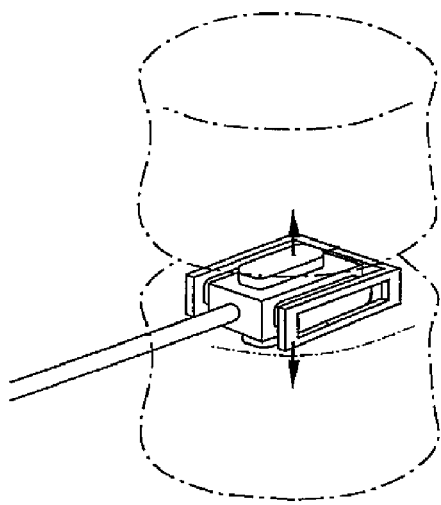
FIG. 7D shows the way in which the intervertebral bodies are "overdistracted" through the action of the instrument.
Figure 7A:
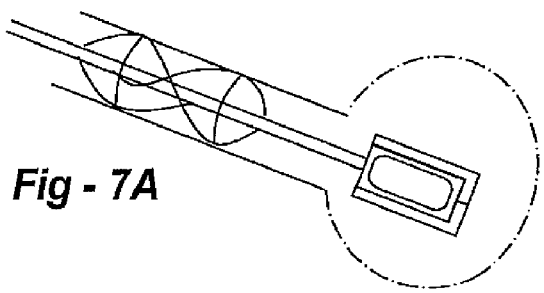
FIG. 7A is a drawing which shows the instrument of FIG. 4, loaded with an expandable cage as shown in FIG. 5, being introduced into an intradiscal space through a cannulated opening.
Figure 7B:
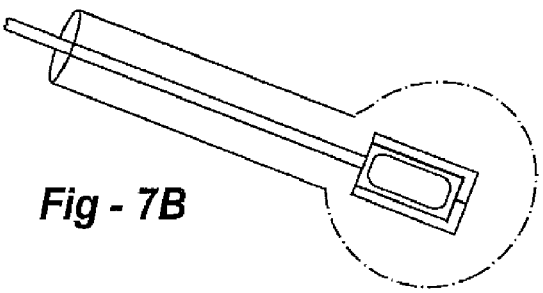
FIG. 7B shows the instrument and cage of FIG. 9A, having been rotated 90 degrees to facilitate overdistraction.
Figure 7E:
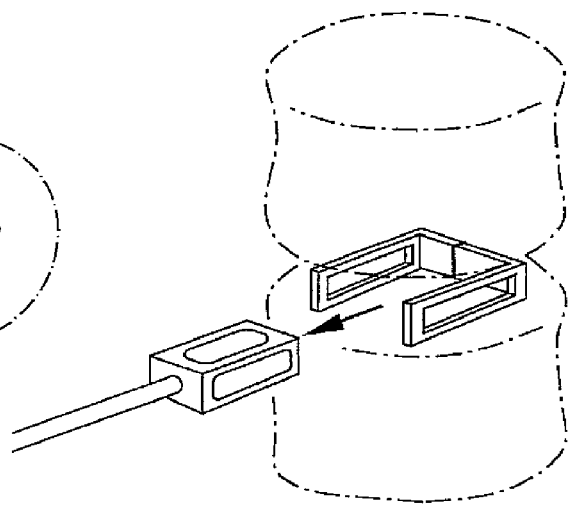
FIG. 7E illustrates the removal of the instrument, leaving the cage in place following the overdistraction.
Figure 7C:
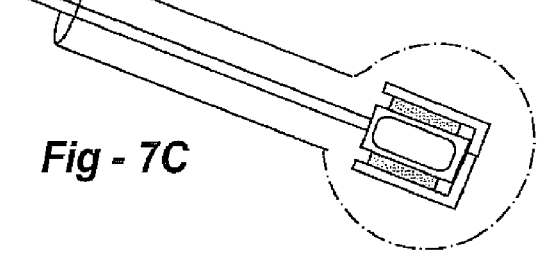
FIG. 7C shows the instrument being deployed, pushing the side walls of the cage outward laterally.

FIG. 7A is a drawing which shows the instrument of FIG. 4, loaded with an expandable cage as shown in FIG. 5, being introduced into an intradiscal space through a cannulated opening. FIG. 7B shows the instrument and cage of FIG. 9A, having been rotated 90 degrees to facilitate overdistraction. FIG. 7C shows the instrument being deployed, pushing the side walls of the cage outward laterally. FIG. 7D shows the way in which the intervertebral bodies are "overdistracted" through the action of the instrument. FIG. 7E illustrates the removal of the instrument, leaving the cage in place following the overdistraction.

Figure 8A:
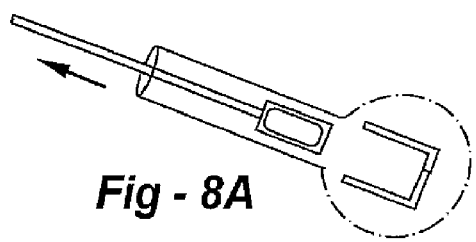
FIG. 8A is a top-down view of instrument removal, leaving a U-shaped cage in position.

FIG. 8A is a top-down view of instrument removal, leaving a U-shaped cage in position. FIG. 8B shows the way in which high speed burrs are used to roughen the endplates. FIG. 8C is a drawing which shows the way biologics may be inserted into the cage prior to closure. These biologics, which may be inserted or injected, include BMP, HEALOS, VITOSS, autograft, allograft, and so forth. FIG. 8D is a drawing which shows the way that autograft/allograft and/or other biologic materials are tamped into the cage prior to closure.

Figure 8E:
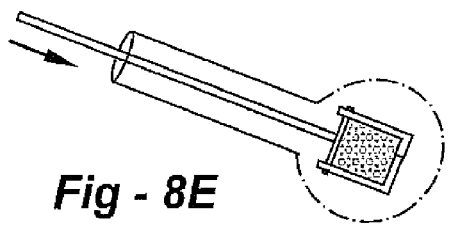
FIG. 8E is a drawing which shows the introduction of the locking gate.
Figure 8B:
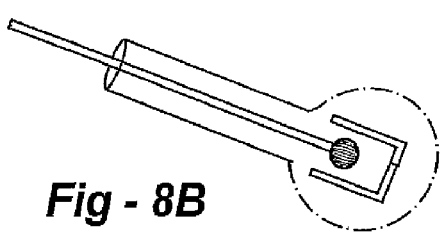
FIG. 8B shows the way in which high speed burrs are used to roughen the endplates.
Figure 8F:
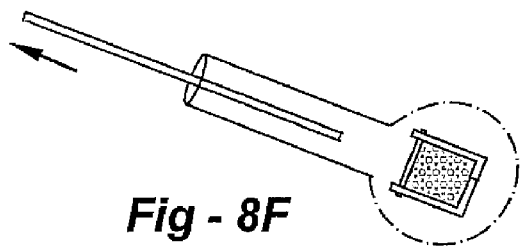
FIG. 8F is a drawing which shows the removal of the gate introduction tool.
Figure 8C:
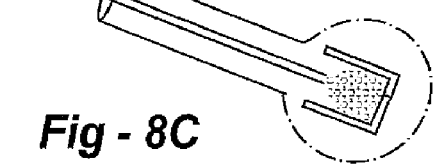
FIG. 8C is a drawing which shows the way biologics may be inserted into the cage prior to closure.
Figure 8D:
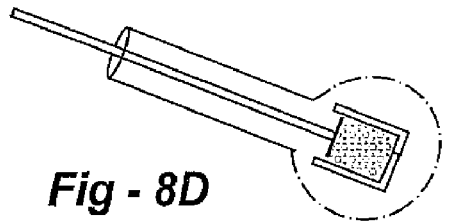
FIG. 8D is a drawing which shows the way that autograft/allograft and/or other biologic materials are tamped into the cage prior to closure.

FIG. 8E is a drawing which shows the introduction of the locking gate using the tool of FIG. 6. The release spring is used to expand the gate and slide it to the outer end of cage where it is clicked into position. FIG. 8F is a drawing which shows the removal of the gate introduction tool. The cannula is removed and the wound is closed. FIG. 9 is a perspective view drawing showing the expanded, filled cage 900 in position between upper and lower vertebral bodies 902, 904.

I claim:

1. Vertebral fusion apparatus, comprising:
    a generally C-shaped cage structure having opposing lateral sides, each with a forward end, a back wall, an open top, an open bottom, and an open front between the forward ends of the lateral sides;
    the back wall being expandable such that the cage structure has a collapsed state with the lateral sides spaced apart at a first distance for insertion into an intervertebral disc space, and an expanded state wherein the lateral sides are spaced apart at a second distance greater than the first distance for packing the cage with bone graft or biological materials; and
    and a locking gate structure having first and second ends that engage with the forward ends of the lateral sides in the expanded state, thereby closing off the open front once packed.

2. The vertebral fusion apparatus of claim 1, wherein the back wall expands through ratcheting.

3. The vertebral fusion apparatus of claim 1, wherein the expandable back wall is comprised of overlapping sections; and
    including a fastener to lock the sections in position in the expanded state.

4. The vertebral fusion apparatus of claim 1, further including a cage introducer instrument having a distal end over which the cage is temporarily held during placement, after which the introducer is removed following placement of the cage.

5. The vertebral fusion apparatus of claim 4, wherein the introducer instrument includes a mechanism to expand the cage in situ.

6. The vertebral fusion apparatus of claim 4, wherein the introducer instrument includes a mechanism to distract the vertebra to ease insertion of the cage.

7. The vertebral fusion apparatus of claim 1, further including a plurality of differently sized cages for different vertebral levels.

8. The vertebral fusion apparatus of claim 1, wherein the gate is expandable.

9. A method of implanting an intervertebral cage, comprising the steps of:
    surgically providing access to in intradiscal space;
    providing the cage of claim 1 in the compressed state;
    inserting the cage into the intradiscal space without the gate;
    expanding the cage into the expanded state;
    packing the cage with bone graft and/or biological materials; and
    closing the cage with the gate.

* * * * *